(12) United States Patent
Ren et al.

(10) Patent No.: US 10,758,889 B2
(45) Date of Patent: Sep. 1, 2020

(54) MEDICAL MACROMOLECULAR MICROSPHERE ADSORBENT FOR A BLOOD PERFUSION APPARATUS AND A PREPARATION METHOD THEREOF

(71) Applicant: South China University of Technology, Guangzhou (CN)

(72) Inventors: Li Ren, Guangzhou (CN); Yingjun Wang, Guangzhou (CN); Sa Liu, Guangzhou (CN); Lin Wang, Guangzhou (CN); Jian Zheng, Guangzhou (CN)

( * ) Notice: Subject to any disclaimer, the term of this patent is extended or adjusted under 35 U.S.C. 154(b) by 327 days.

(21) Appl. No.: 16/001,941

(22) Filed: Jun. 7, 2018

(65) Prior Publication Data

US 2018/0280930 A1 Oct. 4, 2018

Related U.S. Application Data

(63) Continuation of application No. PCT/CN2017/079646, filed on Apr. 7, 2017.

(30) Foreign Application Priority Data

Apr. 8, 2016 (CN) .......................... 2016 1 0218328

(51) Int. Cl.
| | |
|---|---|
| *B01J 20/26* | (2006.01) |
| *B01J 20/28* | (2006.01) |
| *A61M 1/14* | (2006.01) |
| *B01J 20/30* | (2006.01) |

(52) U.S. Cl.
CPC .............. *B01J 20/264* (2013.01); *A61M 1/14* (2013.01); *B01J 20/267* (2013.01); *B01J 20/28004* (2013.01); *B01J 20/28007* (2013.01); *B01J 20/28019* (2013.01); *B01J 20/28057* (2013.01); *B01J 20/28061* (2013.01); *B01J 20/28064* (2013.01); *B01J 20/28066* (2013.01); *B01J 20/3071* (2013.01)

(58) Field of Classification Search
CPC .... B01J 20/26; B01J 20/267; B01J 20/28004; B01J 20/28007; B01J 20/28019; B01J 20/28057; B01J 20/28061; B01J 20/28064; B01J 20/28066; B01J 20/3071; A61M 1/14

USPC .......................................................... 502/10
See application file for complete search history.

(56) References Cited

U.S. PATENT DOCUMENTS

| | | |
|---|---|---|
| 2003/0027879 A1 | 2/2003 | Davankov |
| 2008/0119576 A1 | 5/2008 | Young et al. |
| 2013/0011824 A1 | 1/2013 | Chan et al. |
| 2014/0294751 A1 | 10/2014 | Golobish et al. |

FOREIGN PATENT DOCUMENTS

| | | |
|---|---|---|
| CN | 102344827 A | 2/2012 |
| CN | 102847521 A | 1/2013 |
| CN | 105749886 A | 7/2016 |

OTHER PUBLICATIONS

Zheng, Jian; Research of the Controllable Graft Modification by Polyvinylpyrrolidone on the Material Surface and Its Application; Engineering Master's Dissertation of South China University of Technology; Dec. 28, 2015; Chapter 1, Sections 1.3.3.2 and 1.6.2.1.
International Search Report of PCT/CN2017/079646 dated Jul. 14, 2017.

*Primary Examiner* — Edward M Johnson
(74) *Attorney, Agent, or Firm* — Erson IP (Nelson IP)

(57) ABSTRACT

A medical macromolecular microsphere adsorbent for a blood perfusion apparatus and a preparation method thereof are provided. The polystyrene-divinylbenzene microspheres are graded by different pore sizes and specific surface areas, medically purified, and grafted by a bioactivity-controlled grafting technology. In the microsphere adsorbent, the volume ratio of microspheres with pore sizes of 1-10 μm, 10-100 μm and 100 μm is 1:(1-10):(1-20), the content of residual monomers in the microsphere has $O.D_{190-400\,nm} \leq 0.03$. The microsphere adsorbent not only can adsorb harmful micromolecules in blood but also can effectively adsorb harmful medium-molecules and macromolecules in blood, thereby meeting clinical application demands.

10 Claims, 1 Drawing Sheet

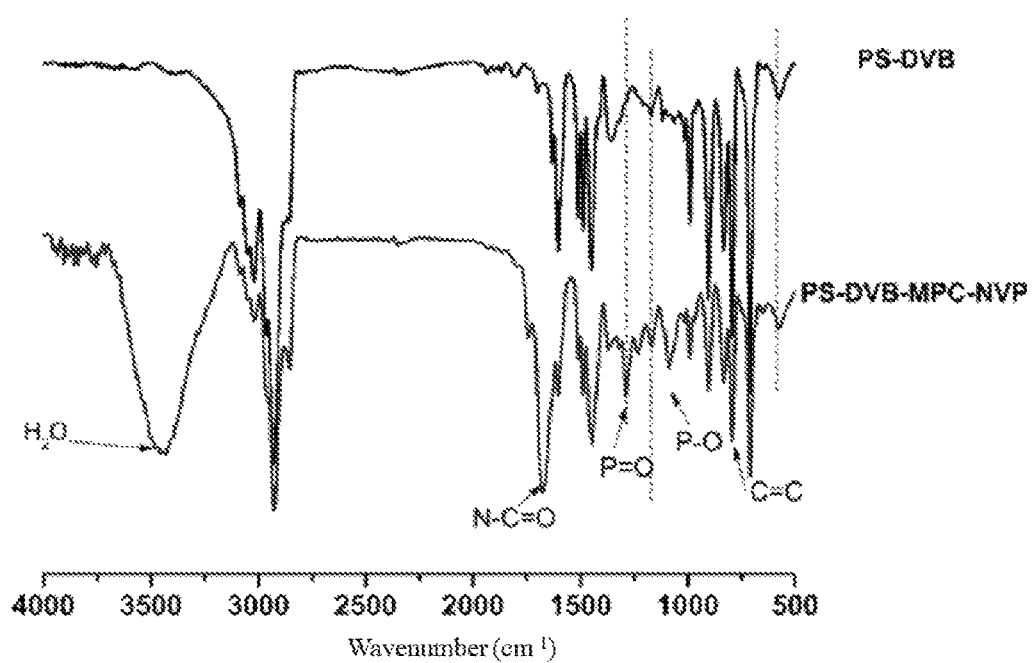

US 10,758,889 B2

MEDICAL MACROMOLECULAR MICROSPHERE ADSORBENT FOR A BLOOD PERFUSION APPARATUS AND A PREPARATION METHOD THEREOF

CROSS-REFERENCE TO RELATED APPLICATIONS

This application is a continuation of International Patent Application No. PCT/CN2017/079646 with a filing date of Apr. 7, 2017, designating the United States, now pending, and further claims priority to Chinese Patent Application No. 201610218328.X with a filing date of Apr. 8, 2016. The content of the aforementioned applications, including any intervening amendments thereto, are incorporated herein by reference.

TECHNICAL FIELD

The disclosure relates to the technical field of blood purification, and particularly relates to a medical macromolecular microsphere adsorbent for a novel blood perfusion apparatus and a preparation method thereof.

BACKGROUND OF THE PRESENT INVENTION

A blood purification technology is a novel medical technology that has been developed on the basis of treatment of chronic renal function failure in the late 20th century. At present, there are about 2000 millions of patients needing blood purification all over the world, and in China, there are about 300 millions of patients. As treatment cost of maintaining blood purification is expensive, only 10% of patients can receive treatment in China at present. Thus, research and development of this technology have a huge potential.

A polystyrene-divinylbenzene microsphere, as the most commonly used medical macromolecular microsphere adsorbent in a blood perfusion apparatus, can adsorb medium-molecular β2 microglobulin in blood to a certain extent. However, the present polystyrene-divinylbenzene microsphere adsorbent used for the blood perfusion apparatus still has the following defects. First, grading design is not performed on pore size, which leads a fact that major adsorption substances are micromolecular substances such as creatinine and pentobarbital which are easy to remove via dialysis, and medium-molecules and macromolecules are difficult to remove. Second, at present, residues of strong irritant chemical substances chloromethyl ether and nitrobenzene are easily caused when neutral macroporous polystyrene-divinylbenzene microspheres are activated in China, so as to bring a great potential safety hazard to health of a patient. Then, blood compatibility of the adsorbent is poor, so red blood cells, leukocytes, blood platelets and the like are destroyed if the adsorbent directly contacts with blood. Thus, how to improve a medical macromolecular microsphere adsorbent is an important research direction of a blood purification technology.

SUMMARY OF PRESENT INVENTION

In view of problems existing in the present blood perfusion apparatus, the object of the disclosure is to provide a medical macromolecular microsphere adsorbent capable of more efficiently removing harmful substances in blood, which can remove medium-molecular and macromolecular harmful substances while effectively removing micromolecular harmful substances in blood.

The object of the disclosure is achieved through the following measures.

A medical macromolecular microsphere adsorbent for a blood perfusion apparatus consists of three polystyrene-divinylbenzene macromolecular microspheres having diameters being 1-10 μm, 10-100 μm and 100-500 μm respectively in a volume ratio of 1:(1-10):(1-20); the surface of the microsphere adsorbent is grafted with vinyl pyrrolidone and/or 2-methylacryloxy ethyl phosphorylcholline; the content of residual monomers in the microsphere adsorbent has O.D190-400 nm≤0.03.

Preferably, the surface area of the microsphere adsorbent is 400 m2/g-1800 m2/g.

A raw material of the polystyrene-divinylbenzene macromolecular microsphere meets regulations of FDA, the mass content of divinylbenzene is larger than 79%, and the polystyrene-divinylbenzene macromolecular microsphere can bear a heavy load of 300-450 g and has a suspension double-bond content of 2.2-3.1 mmol/g.

A method for preparing of the medical macromolecular microsphere adsorbent for the blood perfusion apparatus comprises the following steps:

1) grading of a pore size and a specific surface area of a microsphere adsorbent: separating polystyrene-divinylbenzene microspheres according to diameters being 1-10 μm, 10-100 μm and 10-500 μm respectively; and mixing the microspheres within three size ranges in a volume ratio of 1:(1-10):(1-20);

2) medical purification of the microsphere adsorbent: washing the microsphere adsorbent obtained in step 1) utilizing hydrochloric acid, ammonium hydroxide and ethanol water in turn, and then carrying out rinsing combined treatment and gradient elution on the microsphere adsorbent;

3) grafting a bioactive aglucon on the surface of the microsphere adsorbent utilizing a bioactivity-controlled grafting technology: immersing the microsphere adsorbent purified in step 2) into a bioactive aglucon solution for 1-24 h, the bioactive aglucon being polyvinylpyrrolidone and/or 2-methylacryloxy ethyl phosphorylcholine; then grafting the microsphere under ultraviolet light after being taken out, wherein, the intensity of light is 50 uw/cm2-150 uw/cm2, and grafting time is 1-4 h;

4) posttreatment of the microsphere adsorbent: immersing the grafted microsphere for 1-3 h utilizing buffer solution after being taken out, and washing with deionized water; carrying out freeze drying to obtain the medical macromolecular microsphere adsorbent for the blood perfusion apparatus.

Preferably, the mass concentration of hydrochloric acid is 1%-5%; the mass concentration of ammonium hydroxide is 5%-10%; the mass concentration of ethanol water is 10-20%.

Preferably, the mass concentration of the bioactive aglucon solution is 1%-10%.

Preferably, the ultraviolet light is distanced from a to-be-treated solution by 1 m.

Preferably, the freeze drying is carried out in a freeze drying machine, and the freeze drying time is 12-24 h.

Preferably, the buffer solution is PBS.

Preferably, the number of times of washing with deionized water is 3-10 times.

Polyvinylpyrrolidone (PVP) is a water-soluble macromolecular compound, which has high hydrophilia, excellent biocompatibility and physiological inertness, does not participate in metabolism of a human body, does not form any irritation on skins, mucosa, eyes and the like, and is widely applied to fields closely correlated with human health, such as medicines, food and cosmetics. 2-methylacryloxy ethyl phosphorylcholine (MPC) is a monomer containing a phosphorylcholine (PC) group and has double ionicity, and under a certain condition, its polymes can form a double-molecule layer similar to a biological membrane. In addition, an MPC polymer membrane can effectively inhibit protein adsorption and blood platelet adhesion, can effectively inhibit formation of blood clots and has good blood compatibility. Thus, application of the two compounds to modification of a macromolecular microsphere adsorbent has a wide application prospect.

As compared with the prior art, the disclosure has the following advantages:

1. Grading of a pore size and a specific surface area of a medical macromolecular microsphere adsorbent and a screening technology adopt a macromolecular microsphere produced by a manufacturer accepted by FDA, microspheres having certain pore size distribution and certain mechanical strength and reactivity are screened to ensure that whole blood can smoothly pass through a perfusion apparatus without generating too large resistance, and ensure that the microspheres are not destroyed under a pressure. Grading is performed utilizing macromolecular microspheres having different pore sizes so that the pore size distribution of the microspheres meets separation requirements on toxins having different molecule sizes so as to achieve effective separation of target toxins having different sizes.

2. The graded and screened macromolecular microsphere adsorbent is purified by adopting acid washing, alkaline washing, alcohol washing and rinsing combined treatment process and a gradient elution process to effectively remove residual impurities, so that the microsphere adsorbent achieves requirements on blood purification, use risk is reduced, and safe reliability of product use is improved.

3. A bioactive glucon is grafted to the macromolecular microsphere adsorbent utilizing a bioactivity-controlled grafting technology to introduce a bioactive molecule (for example PVP, MPC) having good blood compatibility on the surface of the macromolecular microsphere, thereby improving blood compatibility of the microsphere, reducing cytomorphosis of red cells and the like and avoiding embolism caused by the microsphere. The removal rate of target toxins is improved utilizing an inter-attractive effect between charges on the bioactive molecule and target toxins while promoting the biocompatibility and blood compatibility of the perfusion apparatus.

DESCRIPTION OF THE DRAWINGS

FIG. 1 is an infrared test diagram before and after the microsphere is grafted with NVP and MPC according to embodiment 1.

DETAILED DESCRIPTION OF PREFERRED EMBODIMENTS

To better understanding the disclosure, the disclosure will be further described in combination with drawings and embodiments below, but, the embodiments of the disclosure are not limited thereto.

Embodiment 1

A polystyrene-divinylbenzene macromolecular microsphere meeting regulations of FDA and containing divinylbenzene whose mass content is larger than 79% is selected as a raw material, and the microsphere can bear a heavy load of 300-450 g and has a suspension double-bond content of 2.2-3.1 mmol/g.

Step 1: Grading of a Pore Size and a Specific Surface Area of the Microsphere Adsorbent (1) Microspheres within three size ranges of 1-10 μm, 10-100 μm and 100-500 μm are mixed in a volume ratio of 1:8:10, and after mixing, the specific surface area is about 951.8 m2/g.

Step 2: Medical Purification of the Microsphere Adsorbent: The Following Washings are Carried Out in Turn (1) The microsphere adsorbent is washed for 2 min utilizing hydrochloric acid having a mass concentration of 2%;

(2) The microsphere adsorbent is washed for 9 min utilizing ammonium hydroxide having a mass concentration of 5%;

(3) The microsphere adsorbent is washed for 2 min utilizing ethanol having a mass concentration of 20%;

(4) The microsphere adsorbent is subjected to rinsing combined treatment and gradient elution.

By detection, the washed microsphere has O.D190-400 nm=0.03

Step 3: Grafting a Bioactive Aglucon on the Surface of the Microsphere Adsorbent Utilizing a Bioactivity-Controlled Grafting Technology.

(1) The microspheres are immersed into a bioactive aglucon solution containing vinyl pyrrolidone (NVP) having a mass concentration of 6% and 2-methylacryloxy ethyl phosphorylcholine (MPC) having a mass concentration of 7% for 16 h;

The structural formula of NVP is:

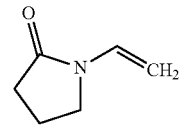

The structural formula of MPC is:

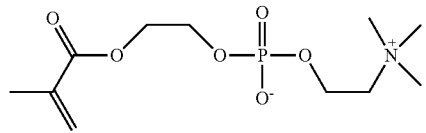

(2) The microspheres are grafted under ultraviolet light after being taken out, wherein, the intensity of the light is 80 uw/cm2 (a position distanced from 1 m), and grafting time is 3 h.

Step 4: Posttreatment of the Microsphere Adsorbent (1) The grafted microspheres are soaked for 3 h utilizing PBS buffer solution after being taken out, and washed 10 times with deionized water;

(2) The microspheres are placed in a freeze drying machine to carry out freeze drying for 18 h, and finally, a novel microsphere adsorbent for a blood perfusion apparatus is obtained.

Test result: an infrared test result before and after the microspheres are grafted is as shown in FIG. 1; specifically, FIG. 1 is a test result diagram obtained by carrying out infrared spectroscopy analysis (a sample is prepared using a tabletting method) on the microsphere sample before and after modification, wherein, PS-DVB represents the polystyrene-divinylbenzene macromolecule microsphere; NVP represents vinyl pyrrolidone; MPC represents 2-methylacryloxy ethyl phosphorylcholine.

In order to illustrate the removal efficiency of the microspheres on toxins in blood, and through this embodiment, removal rates of the modified microspheres on micromolecular toxins creatinine and pentobarbital sodium and medium-molecular toxins B12 and β2 microglobulin are as shown Table 1.

TABLE 1

Removal Rates of Microspheres on Toxins

| Microsphere proportion | Removal rate % | | | |
| --- | --- | --- | --- | --- |
| | Creatinine | Pentobarbital sodium | Vitamin B12 | β2 microglobulin |
| 1:8:10 | 32.15 | 85.18 | 95.23 | 86.31 |

In Table 1, an initial concentration of creatinine is 35 mg/L, an initial concentration of pentobarbital sodium is 80 mg/L, an initial concentration of vitamin B12 is 25 mg/L, and an initial concentration of β2 microglobulin is 1 mg/mL. Table 1 illustrates the adsorbent prepared in this embodiment not only can adsorb harmful micromolecules in blood but also can effectively adsorb harmful medium-molecules and macromolecules in blood so as to meet clinical application demands. At present, application of polystyrene-divinylbenzene microspheres existing on the market to blood perfusion needs to be combined with hematodialysis so as to achieve effective removal of micromolecules and medium-molecules (Sun Tao, comparison of different blood purification manners on toxin removal and dialysis sufficiency [D]; Jilin University; 2009). The microsphere prepared by the disclosure can be applied to blood perfusion, which can be separately used to effectively removing both of micromolecules and medium molecules.

A hemolysis rate represents a destruction degree of a material on red cells in blood when a material applied to biomedicine contacts with blood, and is expressed by measuring degrees of red cell dissolution and hemoglobin dissociation. Test results of hemolysis rates before and after the microspheres are modified are as shown in Table 2. Table 2 lists results of a test carried out according to regulations of International standard GB/T16886.4-2003, and the hemolysis rate is required to be less than 5%.

TABLE 2

Results of Microsphere Hemolysis Rate

| | Samples | | | Average value | Hemolysis rate (%) |
| --- | --- | --- | --- | --- | --- |
| | Sample 1 | Sample 2 | Sample 3 | | |
| Embodiment 1 | 0.024 | 0.022 | 0.023 | 0.023 | 0.82 ± 0.10 |
| Negative control | 0.016 | 0.015 | 0.017 | 0.016 | |
| Positive control | 0.882 | 0.842 | 0.875 | 0.866 | |

Hemolysis rate (HR) is one of extremely important indexes for blood compatibility of a material, and is an important in-vitro coarse screening experiment. A national hemolytic experiment standard of a biomedical material contacting with blood is that a material has a standard hemolysis rate (HR) of <5%. The test illustrates the result of the hemolysis rate of the material prepared by the disclosure is basically similar to that of the product on the market, and achieves the national standard.

Embodiment 2

A polystyrene-divinylbenzene macromolecular microsphere meeting regulations of FDA and containing divinylbenzene whose mass content is larger than 79% is selected as a raw material, and the microsphere can bear a heavy load of 300-450 g and has a suspension double-bond content of 2.2-3.1 mmol/g.

Step 1: Grading of a Pore Size and a Specific Surface Area of the Microsphere Adsorbent (1) Microspheres within three size ranges of 1-10 μm, 10-100 μm and 100-500 μm are mixed in a volume ratio of 1:8:18, and after mixing, the specific surface area is about 578.5 m2/g.

Step 2: Medical Purification of the Microsphere Adsorbent (1) The microsphere adsorbent is washed for 1 min utilizing hydrochloric acid having a mass concentration of 5%;

(2) The microsphere adsorbent is washed for 8 min utilizing ammonium hydroxide having a mass concentration of 10%;

(3) The microsphere adsorbent is washed for 19 min utilizing ethanol having a mass concentration of 10%;

(4) The microsphere adsorbent is subjected to rinsing combined treatment and gradient elution.

After washing, O.D190-400 nm=0.025.

Step 3: A Bioactive Aglucon is Grafted on the Surface of the Microsphere Adsorbent Utilizing a Bioactivity-Controlled Grafting Technology.

(1) The microspheres are immersed into a bioactive aglucon solution containing vinyl pyrrolidone (NVP) having a mass concentration of 7% and 2-methylacryloxy ethyl phosphorylcholine (MPC) having a mass concentration of 2% for 12 h;

(2) The microspheres are grafted under ultraviolet light after being taken out, wherein, the intensity of the light is 100 uw/cm2 (a position distanced from 1 m), and grafting time is 1 h.

Step 4: Posttreatment of the Microsphere Adsorbent (1) The grafted microspheres are soaked for 1 h utilizing PBS buffer solution by being taken out, and washed 8 times with deionized water;

(2) The microspheres are placed in a freeze drying machine to carry out freeze drying for 20 h, and finally, a novel microsphere adsorbent for a blood perfusion apparatus is obtained.

Embodiment 3

A polystyrene-divinylbenzene macromolecular microsphere meeting regulations of FDA and containing divinylbenzene whose mass content is larger than 79% is selected as a raw material, and the microsphere can bear a heavy load of 300-450 g and has a suspension double-bond content of 2.2-3.1 mmol/g.

Step 1: Grading of a Pore Size and a Specific Surface Area of the Microsphere Adsorbent (1) Microspheres within three size ranges of 1-10 μm, 10-100 μm and 100-500 μm are mixed in a volume ratio of 1:5:12, and after mixing, the specific surface area is about 732.5 m2/g.

Step 2: Medical Purification of the Microsphere Adsorbent (1) The microsphere adsorbent is washed for 10 min utilizing hydrochloric acid having a mass concentration of 1%;

(2) The microsphere adsorbent is washed for 10 min utilizing ammonium hydroxide having a mass concentration of 7%;

(3) The microsphere adsorbent is washed for 20 min utilizing ethanol having a mass concentration of 12%;

(4) The microsphere adsorbent is subjected to rinsing combined treatment and gradient elution.

After washing, $O.D_{190\text{-}400\ nm}=0.01$

Step 3: A Bioactive Aglucon is Grafted on the Surface of the Microsphere Adsorbent Utilizing a Bioactivity-Controlled Grafting Technology.

(1) The microspheres are immersed into a bioactive aglucon solution containing vinyl pyrrolidone (NVP) having a mass concentration of 3% and 2-methylacryloxy ethyl phosphorylcholine (MPC) having a mass concentration of 2% for 24 h;

(2) The microspheres are grafted under ultraviolet light after being taken out, wherein, the intensity of the light is 150 uw/cm2 (a position distanced from 1 m), and grafting time is 4 h.

Step 4: Posttreatment of the Microsphere Adsorbent (1) The grafted microspheres are soaked for 3 h utilizing PBS buffer solution after being taken out, and washed 5 times with deionized water;

(2) The microspheres are placed in a freeze drying machine to carry out freeze drying for 14 h, and finally, a novel microsphere adsorbent for a blood perfusion apparatus is obtained.

The test results of removal effects of novel medical macromolecular microsphere adsorbents for the blood perfusion apparatus obtained in embodiment 2 and embodiment 3 on micromolecular toxins creatinine and pentobarbital sodium and medium-molecular toxins vitamin B12 and β2 microglobulin are as shown in Table 3.

TABLE 3

| | Removal rate % | | | |
|---|---|---|---|---|
| Embodiments | Creatinine | Pentobarbital sodium | Vitamin B12 | β2 microglobulin |
| Embodiment 2 | 91 | 52 | 25 | 34 |
| Embodiment 3 | 13 | 20 | 29 | 62 |

We claim:

1. A medical macromolecular microsphere adsorbent for a blood perfusion apparatus, wherein the microsphere adsorbent consists of three polystyrene-divinylbenzene microspheres having diameters being 1-10 μm, 10-100 μm and 100-500 μm respectively in a volume ratio of 1:(1-10):(1-20); the surface of the microsphere adsorbent is grafted with vinyl pyrrolidone and/or 2-methylacryloxy ethyl phosphorylcholline; the content of residual monomers in the microsphere adsorbent has O.D190-400 nm≤0.03.

2. The medical macromolecular microsphere adsorbent for a blood perfusion apparatus according to claim 1, wherein the surface area of the microsphere adsorbent is 400 m²/g-1800 m²/g.

3. The medical macromolecular microsphere adsorbent for a blood perfusion apparatus according to claim 1, wherein a raw material of the polystyrene-divinylbenzene macromolecular microsphere meets regulations of FDA, the mass content of divinylbenzene is larger than 79%, and the polystyrene-divinylbenzene macromolecular microsphere can bear a heavy load of 300-450 g and has a suspension double-bond content of 2.2-3.1 mmol/g.

4. A method for preparing for a medical macromolecular microsphere adsorbent for a blood perfusion apparatus according to claim 1, characterized by comprising the following steps:

1) grading of a pore size and a specific surface area of a microsphere adsorbent: separating polystyrene-divinylbenzene macromolecular microspheres according to diameters being 1-10 μm, 10-100 μm and 100-500 μm respectively; and mixing the microspheres within three size ranges in a volume ratio of 1:(1-10):(1-20);

2) medical purification of the microsphere adsorbent: washing the microsphere adsorbent obtained in step 1) utilizing hydrochloric acid, ammonium hydroxide and ethanol water in turn, and then carrying out rinsing combined treatment and gradient elution on the microsphere adsorbent;

3) grafting a bioactive aglucon on the surface of the microsphere adsorbent utilizing a bioactivity-controlled grafting technology: immersing the microsphere adsorbent purified in step 2) into a bioactive aglucon solution for 1-24 h, the bioactive aglucon being polyvinylpyrrolidone and/or 2-methylacryloxy ethyl phosphorylcholine; and then grafting the microsphere under ultraviolet light after being taken out, wherein, the intensity of light is 50 uw/cm2-150 uw/cm2, and grafting time is 1-4 h; and 4) posttreatment of the microsphere adsorbent: immersing the grafted microsphere for 1-3 h utilizing buffer solution after being taken out, and washing with deionized water; carrying out freeze drying to obtain the medical macromolecular microsphere adsorbent for the blood perfusion apparatus.

5. The method for preparing for a medical macromolecular microsphere adsorbent for a blood perfusion apparatus according to claim 4, wherein the mass concentration of hydrochloric acid is 1%-5%; the mass concentration of ammonium hydroxide is 5%-10%; the mass concentration of ethanol water is 10-20%.

6. The method for preparing for a medical macromolecular microsphere adsorbent for a blood perfusion apparatus according to claim 4, wherein the mass concentration of the bioactive aglucon solution is 1%-10%.

7. The method for preparing for a medical macromolecular microsphere adsorbent for a blood perfusion apparatus according to claim 4, wherein the ultraviolet light is distanced from the to-be-treated solution by 1 m.

8. The method for preparing for a medical macromolecular microsphere adsorbent for a blood perfusion apparatus according to claim 4, wherein the freeze drying is carried out in a freeze drying machine, and the freeze drying time is 12-24 h.

9. The method for preparing for a medical macromolecular microsphere adsorbent for a blood perfusion apparatus according to claim 4, wherein the buffer solution is phosphate buffer saline (PBS).

10. The method for preparing for a medical macromolecular microsphere adsorbent for a blood perfusion apparatus according to claim 4, wherein the number of times of washing with deionized water is 3-10 times.

* * * * *